United States Patent
Ahmad et al.

(10) Patent No.: US 7,282,583 B2
(45) Date of Patent: Oct. 16, 2007

(54) PROCESS FOR MAKING 5,11-DIHYDRO-11-ETHYL-5-METHYL-8{2-{(1-OXIDO-4-QUINOLINYL)OXY}ETHYL}-6H-DI PYRIDO[3,2-B:2',3'-E][1,4]DIAZEPIN-6-ONE

(75) Inventors: Saeed Ahmad, Chester, VA (US); Robert Frederick Boswell, Jr., Richmond, VA (US); Jack Delbert Brown, Moseley, VA (US); Cary Mark Davis, Richmond, VA (US); Kai Oliver Donsbach, Glen Allen, VA (US); Bernard Franklin Gupton, Midlothian, VA (US); Christopher Peter Johnson, III, Richmond, VA (US); Ahmad Khodabocus, Richmond, VA (US); Vithalanand R. Kulkarni, Richmond, VA (US); Young S. Lo, Chester, VA (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/560,536

(22) Filed: Nov. 16, 2006

(65) Prior Publication Data

US 2007/0129542 A1    Jun. 7, 2007

Related U.S. Application Data

(60) Provisional application No. 60/742,405, filed on Dec. 5, 2005.

(51) Int. Cl.
C07D 471/14    (2006.01)
C07D 215/16    (2006.01)
C07D 211/72    (2006.01)
C07D 211/84    (2006.01)

(52) U.S. Cl. ............. 540/495; 546/153; 546/310; 546/316

(58) Field of Classification Search ............. 540/495; 546/153, 310, 316
See application file for complete search history.

(56) References Cited

U.S. PATENT DOCUMENTS

| 5,856,531 A | 1/1999 | Beavers |
| 6,229,041 B1 | 5/2001 | Brown et al. |
| 6,420,359 B1 | 7/2002 | Simoneau |
| 6,759,533 B2 | 7/2004 | Busacca et al. |
| 2002/0028807 A1 | 3/2002 | Simoneau |
| 2006/0100200 A1 | 5/2006 | Meyer et al. |

FOREIGN PATENT DOCUMENTS

| WO | 9817658 | 4/1998 |
| WO | 0196338 A1 | 12/2001 |
| WO | 2004002989 A1 | 1/2004 |

OTHER PUBLICATIONS

Jones, et al; New Methods of Synthesis of β-Aminoethylpyrazoles; Journal of American Chemical Society; 1953; vol. 75; pp. 4048-4052.
Fairfull-Smith; Synthetic and Mechanistic Investigations of Some Novel Organophosphorus Reagents; School of Science, Faculty of Science, Griffith University; May 2004; Submitted in fulfilment of the requirements of the Degree of Doctor of Philosophy.
Herr; A Wirlwind Tour of Current Mitsunobu Chemistry; Albany Molecular Research, Inc.; Technical Reports; vol. 3, No. 19; 1999; Albany, NY.
Phase Transfer Catalysis; Sigma-Aldrich Co; 2005.

*Primary Examiner*—Bruck Kifle
(74) *Attorney, Agent, or Firm*—Michael P. Morris; Mary-Ellen M. Devlin; Alan R. Stempel

(57) ABSTRACT

An improved process for making 5,11-dihydro-11-ethyl-5-methyl-8-{2-{(1-oxido-4-quinolinyl)oxy}ethyl}-6H-di pyrido[3,2-b:2',3'-e][1,4]diazepin-6-one.

16 Claims, No Drawings

PROCESS FOR MAKING 5,11-DIHYDRO-11-ETHYL-5-METHYL-8{2-{(1-OXIDO-4-QUINOLINYL)OXY}ETHYL}-6H-DI PYRIDO[3,2-B:2',3'-E][1,4]DIAZEPIN-6-ONE

RELATED APPLICATIONS

Benefit of U.S. provisional application Ser. No. 60/742,405 filed on Dec. 5, 2005 is hereby claimed.

TECHNICAL FIELD OF THE INVENTION

The invention relates to a novel process for making 5,11-Dihydro-11-ethyl-5-methyl-8-{2-{(1-oxido-4-quinolinyl)oxy}ethyl}-6H-di pyrido[3,2-b:2',3'e][1,4]diazepin-6-one.

BACKGROUND OF THE INVENTION 5,11-Dihydro-11-ethyl-5-methyl-8-{2-{(1-oxido-4-quinolinyl)oxy}ethyl}-6H-di pyrido[3,2-b:2',3'-e][1,4]diazepin-6-one is a known per se HIV-RT inhibitor. The synthesis and method for use of this compound in the treatment of HIV is taught by U.S. Pat. No. 6,420,359 and the corresponding International Application WO0196338.

An alternative synthesis is described by U.S. Pat. No. 6,759,533 and the corresponding WO2004002989.

SUMMARY OF THE INVENTION

The invention provides an improved process for making 5,11-dihydro-11-ethyl-5-methyl-8-{2-{(1-oxido-4-quinolinyl)oxy}ethyl}-6H-di pyrido[3,2-b:2',3'-e][1,4]diazepin-6-one; that is to say, the compound having the following structural formula:

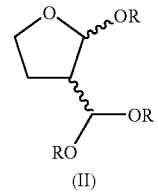

DETAILED DESCRIPTION OF THE INVENTION

The novel synthetic route provided by the invention can be understood in its broadest sense by the following step by step description of the process.

Step 1: Synthesis of 2-alkyloxy-tetrahydrofuran-3-carbaldehyde dialkylacetal

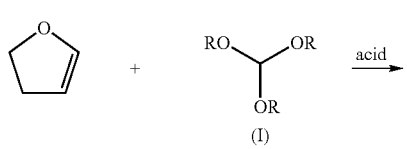

In the initial step of the process according to the invention 2,3-dihydrofuran is reacted with a trialkylorthoformate of the formula I,

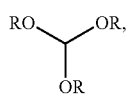

wherein each of the groups R is selected independently and is an alkyl of 1 to 6 carbon atoms, phenyl or cycloalkyl group of 3 to 6 carbon atoms, in the presence of a catalytic amount of an acid, to yield an intermediate of the formula II,

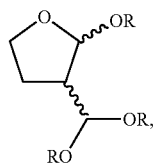

wherein R is as hereinbefore defined.

In the starting material of the formula I it is preferred that all of the groups R be the same, although they can be different. Thus, the starting material of the formula I can be, for example, trimethylorthoformate, triethylorthoformate, tripropylorthoformate or dimethylethylorthoformate. The use of trimethylorthoformate is preferred.

A variety of acids may be used to catalyze the first reaction step. The acid should be at least moderately strong. Preferred are the Lewis acids such as, for example, lithium chloride, lithium perchlorate, zinc chloride, trimethylsilyltriflate, aluminum chloride, zinc bromide, and boron trifluoride etherate. The preferred Lewis acid is boron trifluoride etherate. Bronsted-Lowry acids can also be employed. For example, inorganic acids such as HCl and, $H_2SO_4$, and organic carboxylic acids such as acetic acid or benzoic acid and halogenated carboxylic acids can be employed.

The reaction is preferably carried out neat, although it may be run in an inert organic solvent. It is crucial that the reaction be carried out in the absence of water.

The reaction is preferably but not necessarily carried out under an inert atmosphere.

Before going on the reaction is preferably quenched with a strong base such as, for example, NaOH, in a suitable solvent, such as, for example, methanol.

The intermediate product of the formula II, which is a mixture of diastereomers, is isolated from the reaction mixture. Those of ordinary skill in the art will understand that various isolation techniques may be employed for this purpose. Filtration followed by distillation is the preferred method. For example, chromatography, TLC or HPLC are also possible.

Step 2: Synthesis of Penta-2,4-dienenitrile

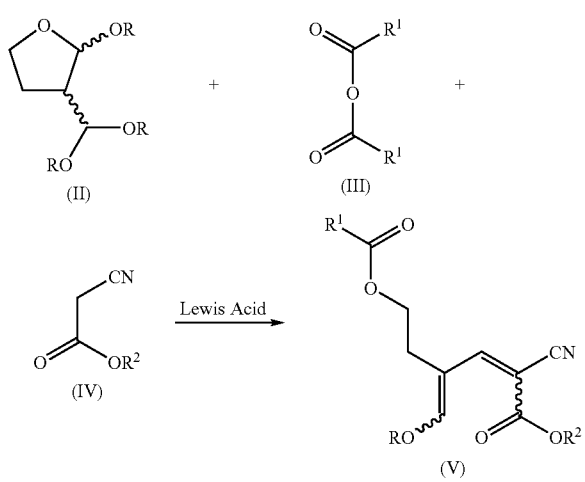

In the second process step, the intermediate of the formula II, formed in the preceding step, is reacted with an acid anhydride of the formula III,

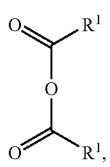
(III)

wherein each $R^1$ group is an alkyl group of 2 to 6 carbon atoms, cycloalkyl of 3 to 6 carbon atoms, phenyl or benzyl, in the presence of a catalytic amount of a Lewis acid, and with an alkylcyanoacetate of the formula IV,

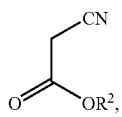
(IV)

wherein $R^2$ is an alkyl group of 2 to 6 carbon atoms, cycloalkyl of 3 to 6 carbon atoms, phenyl or benzyl, to yield a substituted penta-2,4-dienenitrile intermediate of the formula V,

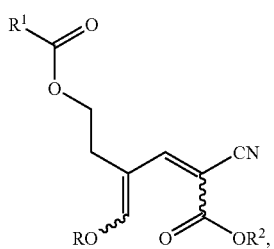
(V)

wherein the groups R, $R^1$ and $R^2$ are as hereinbefore defined.

The reaction is carried out at elevated temperature, preferably at reflux, under an inert atmosphere.

The substituted penta-2,4-dienenitrile intermediate of the formula V is isolated with techniques state of the art like distillation, extraction, crystallization, chromatography or combinations thereof from the reaction mixture before going on to the next step.

The Lewis acid may be, by way of non-limiting example, lithium chloride, lithium perchlorate, trimethylsilyltriflate, aluminum chloride, borontrifluoride, iron chloride, iron bromide, zinc bromide or zinc chloride with the latter being preferred.

The above reaction step may be carried out neat or in a suitable solvent, which may be any aprotic solvent which is stable toward acids, such as, for example, dichloromethane, methyl isobutyl ketone or ethers such as diethyl ether.

Step 3: Synthesis of Substituted Pyridine

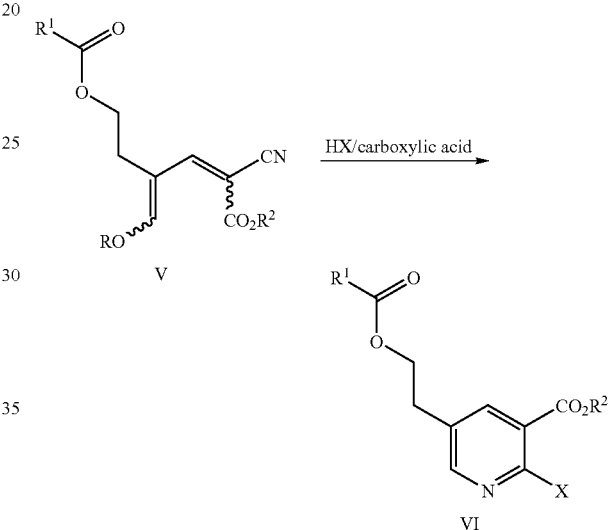

The substituted penta-2,4-dienenitrile intermediate of the formula V, obtained from the prior step, is next dissolved in a suitable carboxylic acid, preferably acetic acid, and treated with an anhydrous acid of the formula HX, wherein X is a halogen atom, to yield a substituted pyridine of the formula VI

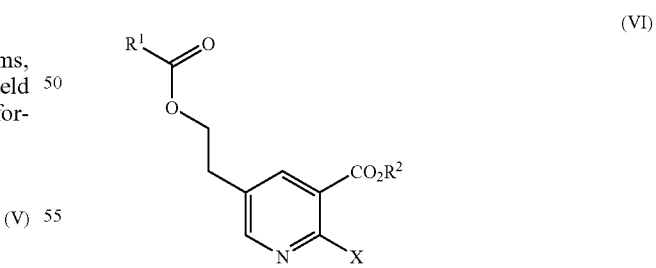
(VI)

wherein $R^1$, $R^2$ and X are as hereinbefore defined.

The reaction is preferably but not necessarily carried out under an inert atmosphere.

Exemplary anhydrous acids which may be used in this step are hydrogen chloride, hydrogen bromide and hydrogen iodide. The use of hydrogen bromide is preferred.

Isolation of the substituted pyridine of the formula VI before going on to the next step is optional.

Step 4: Saponification of the Substituted Pyridine

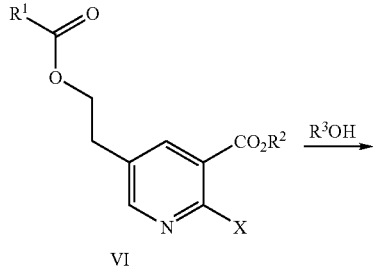

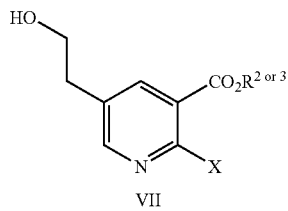

The substituted pyridine of the formula VI, obtained from the previous step, is next treated with an alcohol of the formula R³OH, wherein R³ is preferably an alkyl group of 2 to 6 carbon atoms, cycloalkyl of 3 to 6 carbon atoms, phenyl or benzyl, to yield a saponified intermediate of the formula VII

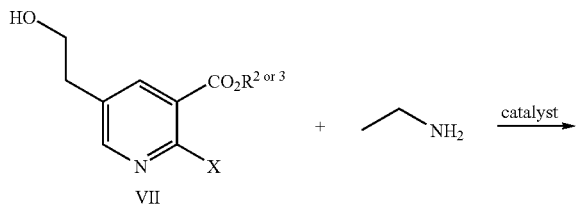

wherein $R^2$, $R^3$ and X are as hereinbefore defined. (It should be understood that transesterification can take place during this reaction step. Accordingly, if $R^2$ and $R^3$ are different, the intermediate of formula VII can be a mixture of different esters. To connote this possibility, the notation $R^{2\ or\ 3}$ is employed in the above reaction scheme and means that the ester moiety can be either —$CO_2R^2$ or —$CO_2R^3$.)

As mentioned above, isolation of the substituted pyridine of the formula VI is optional. The alcohol may simply be added to the reaction mixture of the previous step. Alternatively, the solvent from the previous step may first be removed, as by distillation, prior to addition of the alcohol.

Before going on to the next step, the intermediate product of the formula VII is worked up and isolated in a manner which will be apparent to those of ordinary skill in the art.

Step 5: Amination of the Substituted Pyridine

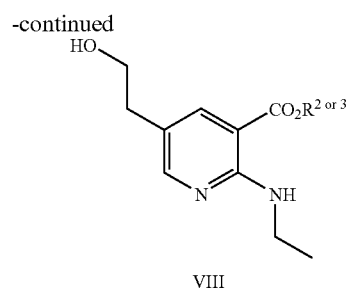

The substituted pyridine of the formula VII, obtained from the preceding step, is next reacted with ethylamine, in the presence of a catalyst, to yield an aminated intermediate of the formula VIII

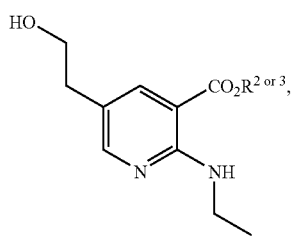

wherein $R^{2\ or\ 3}$ is as hereinbefore defined.

Suitable catalysts are transition metal catalysts such as, for example, copper (I) chloride, copper (I) bromide, copper (I) iodide, copper (I) triflate, copper (I) oxide, copper (II) chloride, copper (II) bromide, copper (II) iodide and copper (II) oxide or palladium catalysts. Copper (I) bromide is preferred.

The reaction is run in an appropriate organic solvent such as, for example, ethanol, methanol, isopropanol, Dimethoxyether, THF, MTBE, Diglyme, DMF or DMSO. THF is preferred.

The intermediate of the formula VIII is optionally isolated by means which will be apparent to one of ordinary skill in the art before going on to the next step.

Step 6: Coupling of the Pyridine to 4-hydroxyquinoline

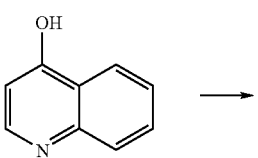

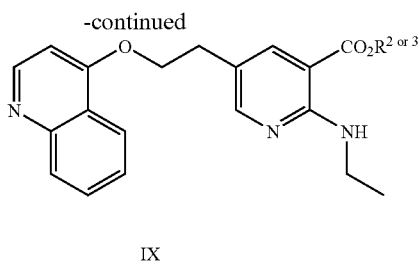

IX

The intermediate of the formula VIII obtained from the previous step is next reacted with 4-hydroxyquinoline, in the presence of a reagent which generates a suitable leaving group from the alcoholic moiety of the compound of the formula VIII, to yield an intermediate of the formula IX

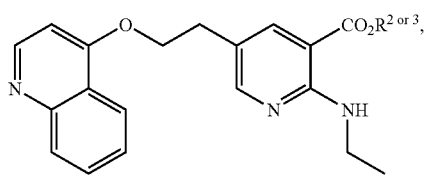

wherein $R^{2\ or\ 3}$ is as hereinbefore defined. Suitable reagents are, for example, sulfonyl chlorides such as para-Toluene sulfonic acid or Methyl-sulfonic acid or Mitsunobu conditions wherein a reducing and an oxidizing reagent are used. Exemplary reducing Mitsunobu reagents are trisubstituted phosphorus compounds such as trialkylphosphines (such as tributylphosphine and trimethylphosphine), the trialkyl phosphites (such as trimethyl phosphite, triethyl phosphate and tributyl phosphate), and the triarylphosphines (such as triphenylphosphine), preferably triphenylphosphine. Exemplary oxidizing Mitsunobu reagents are azidocarbonyl compounds such as the dialkylazodicompound (such as diethylazodicarboxylate, diisopropylazodicarboxylate, 3-(N,N-dimethylcarbamoylimido)-1,1-dimethylurea, N,N,N',N'-tetraisopropylazodicarboxamide), most preferably diisopropylazodicarboxylate (DIAD).

To perform this condensation reaction the intermediate of the formula VIII is first dissolved in a suitable organic solvent. Exemplary solvents are THF, DME, Diglyme, toluene, ethylacetate and isopropyl acetate, with DME or THF being preferred. It is preferred to use Mitsunobu conditions to convert the hydroxyl group to a leaving group.

Before going on to the next step the intermediate of formula IX is optionally worked up to yield a crude product. Those skilled in the art will appreciate how such workup may be performed.

Step 7: Hydrolysis of the Ester Intermediate of Formula IX

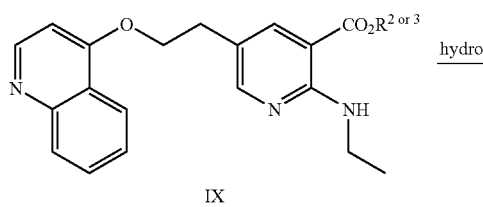

IX

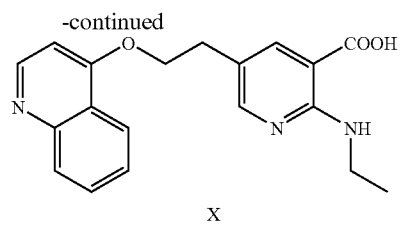

X

The ester intermediate of the formula IX, obtained from the previous step, is next hydrolyzed to yield the carboxylic intermediate of the formula X

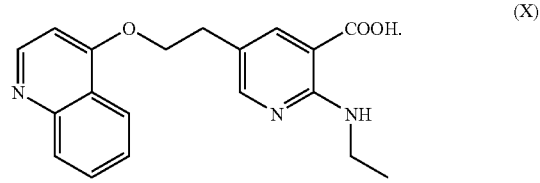

Those skilled in the art will know how to perform this hydrolysis. Although acid-catalyzed hydrolysis may be employed, it is preferred to employ base-catalyzed hydrolysis wherein the ester IX is treated with a metal hydroxide (lithium hydroxide, sodium hydroxide, potassium hydroxide, magnesium hydroxide, calcium hydroxide, preferably with sodium hydroxide) in a alcoholic solvent (methanol, ethanol, propanol, isopropanol, butanol, preferably with methanol) or in water or a mixture of alcohol and water to give the desired carboxylic acid of formula X after pH adjustment.

The intermediate of the formula X is isolated from the reaction mixture before going on to the next step. Those skilled in the art will understand that there are various ways to perform this isolation. If Mitsunobu conditions were employed it is preferred to wash the reaction mixture with an immiscible organic solvent, such as for example toluene, isopropyl acetate or methyl isobutyl ketone, which removes the triphenylphosphine oxide. The organic phase is removed and the pH is adjusted to acidic conditions, the organic phase is replaced and the product is then transferred to the organic phase.

Step 8: Formation of Activated Acid

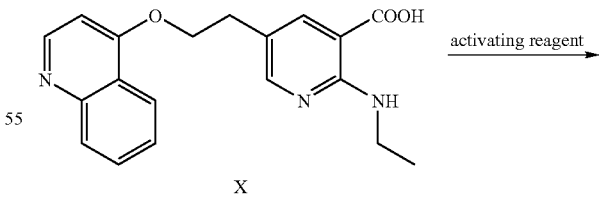

X

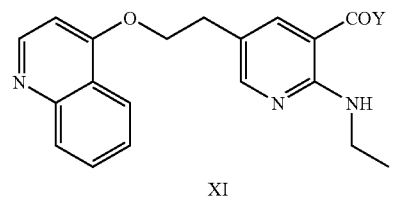

XI

The carboxylic acid intermediate of the formula X, obtained from the previous step, is next reacted with an activating agent, to yield the activated acid of the formula XI

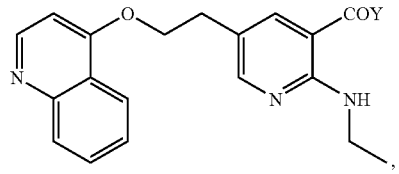

wherein Y is $OR^4$ (wherein $OR^4$ is a leaving group such as OBt (1-hydroxybenzotriazole), ONSu (N-hydroxysuccinimide) or OPFP (pentafluorophenol)), or $O_2CR^5$ (wherein $R^5$ is an alkyl group of 2 to 6 carbon atoms, cycloalkyl of 3 to 6 carbon atoms, phenyl or benzyl) or a halogen.

The activating agent can be any reagent which facilitates the transformation of the acid to an activated carboxylic acid, which can in turn be converted to an amide.

Exemplary activating agents would be peptide coupling reagents, which lead to activated esters (Y=acid anhydrides which lead to mixed anhydrides or halogenating reagents such as phosphorous oxychloride, phosphorous trichloride, phosphorous pentachloride, cyanuric chloride, oxalylchloride and thionyl chloride, with the later being preferred.

This reaction is carried out in an appropriate organic solvent such as toluene, xylene, Dichloroethane, methylene chloride, THF, DME, Diglyme, DMF, DMAc, NMP or acetonitrile, with the latter being preferred.

Step 9: Introduction of Second Pyridine Ring

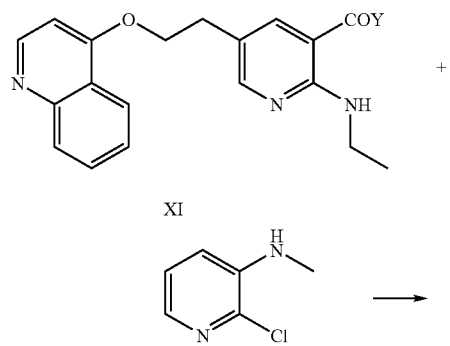

The activated acid of the formula XI, obtained from the previous step, is next reacted with 2-chloro-3-methylaminopyridine, to yield a further intermediate of the formula XII

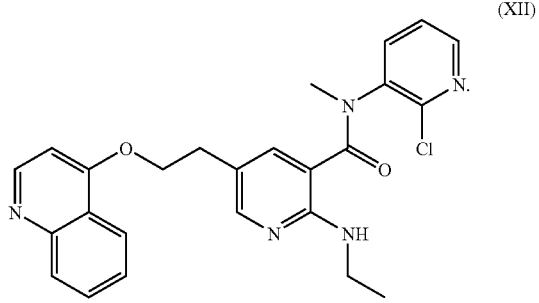

This reaction is carried out in an appropriate organic solvent such as toluene, xylene, Dichloroethane, methylene chloride, THF, DME, Diglyme, DMF, DMAc, NMP or acetonitrile, with the latter being preferred.

The intermediate of the formula XII is isolated in a conventional manner before going on to the next step. Preferably the crude reaction mixture is quenched with aqueous sodium hydroxide, and crystallized from isopropyl acetate.

Step 10: Formation of the Diazepine Ring

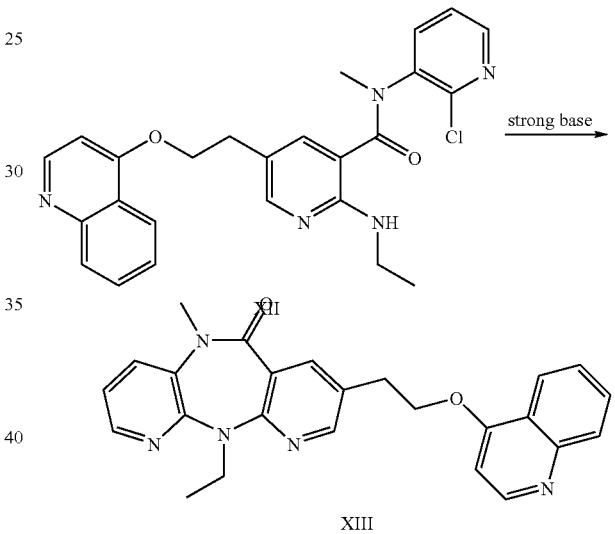

The intermediate of the formula XII, obtained from the previous step is next treated with base, which induces ring closure and yields the intermediate of the formula XIII Those skilled in the art will understand that there are a variety of ways to conduct this base-catalyzed ring closure. However, it is preferred to utilize phase transfer catalysis. For example, the intermediate of the formula XII can be dissolved in a suitable organic solvent (which can be, by way of non-limiting example, methylene chloride, THF, acetonitrile or toluene), along with a phase transfer catalyst (which can be, by way of non-limiting example, tetraalkylammonium halide, for example tetraethylammonium halide, tetramethylammonium halide, tetrabutylammonium halide, tetrabutylammonium halide, triethylbenzylammonium halide). This organic phase is then treated with a base or an aqueous solution thereof, which will typically be a metal hydroxide (which can be, by way of non-limiting example, lithium hydroxide, potassium hydroxide, magnesium hydroxide, calcium hydroxide, cesium hydroxide or sodium hydroxide), metal carbonate (such as lithium, sodium, potassium or cesium carbonate) or metal phosphate (such as lithium, sodium, potassium phosphates and hydrogen phosphates).

The intermediate of the formula XIII is worked up and crystallized before going on to the next step.

Step 11: Oxidation to N-oxide

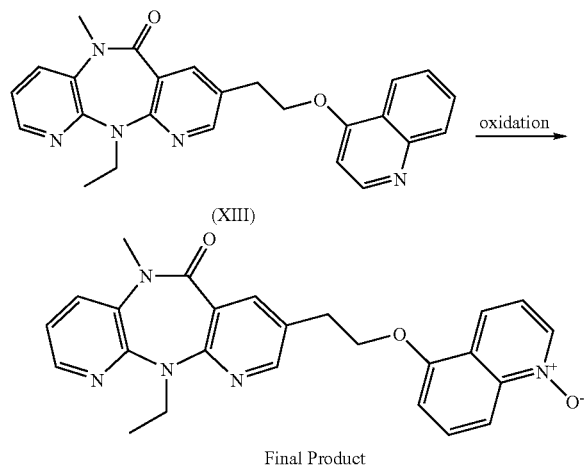

(XIII)

Final Product

In the final process step the intermediate of the formula XIII is treated with an oxidizing agent to yield the final product, 5,11-dihydro-11-ethyl-5-methyl-8-{2-{(1-oxido-4-quinolinyl)oxy}ethyl}-6H-di pyrido[3,2-b:2',3'-e][1,4]diazepin-6-one.

Those of skill in the art will appreciate that this oxidation may be accomplished in various ways. For example, the penultimate quinoline intermediate can be treated with mCPBA, as described in U.S. Pat. No. 6,420,359 (see reaction scheme 5).

The invention may be further understood by means of the following example, which describes a specific synthesis of the penultimate intermediate, 5,11-dihydro-11-ethyl-5-methyl-8-{2-(4-quinolinyloxy)ethyl}-6H-dipyrido[3,2-b:2',3'-e][1,4]diazepin-6-one.

EXAMPLE 1

Step 1: Production of 3-(Dimethoxymethyl)-2-methoxyoxolane

Into a dried 3L three neck-round bottom flask with a stirrer bar, nitrogen-inlet, thermocouple and a 1L-addition funnel was charged 1227.2 g (11.56 mol) of trimethylorthoformate, which was cooled to −5° C. to −3° C. while agitating. The reaction mixture was charged with 3.855 g BF$_3$.Et$_2$O (21 mmol) while agitating under nitrogen. The addition funnel was then charged with a mixture of 315.41 g 2,3-dihydrofurane (4.5 mol) and 434.64 g trimethylorthoformate (4.1 mol) and this mixture was added to the reaction mixture over a period of 160-180 minutes while maintaining the temperature at −5° to −3° C. After the addition was complete, the reaction was quenched with 3.24 g NaOH (81 mmol) in 12.96 g MeOH and left 16 h at 15° C. The reaction mixture was filtered and distilled first under atmospheric pressure, then under reduced pressure. The intermediate product obtained boils at 79-85° C. at 6.8-6.9 mmHg and is a mixture of diastereomers.

Yield: 702.61 g (89%), colorless oil.

Step 2: Production of Methyl-4-(2-acetyloxyethyl)-2-cyano-5-methoxypenta-2,4-dienoate Into a dried 3L three neck-round bottom flask with a stirrer bar, nitrogen-inlet, thermocouple and a addition funnel were charged 150 g (851.26 mmol) 3-(dimethoxymethyl)-2-methoxyoxolane, 355.27 g (3.48 mol) Ac$_2$O and 2.12 g (15.55 mmol) ZnCl$_2$ and the mixture was heated for 1.25-1.5 h at 100-120° C. to reflux. The solution started to become brown and a small portion of solvent was distilled off at atmospheric pressure. To the reaction mixture 76.7 g (774 mmol) methylcyanacetate was slowly added over 1 h while continuing to distill off solvent. After the addition was completed, the reaction mixture was evacuated and the residual solvent was distilled off. The residue was treated with 224 g MeOH and again evacuated and the solvent was distilled off. The residual black oil was charged with 500 ml CH$_2$Cl$_2$ and washed twice with 500 ml water. The solvent was distilled off under reduced pressure and the residue was treated with a mixture of 350 ml MTBE and 285 ml heptane. The reaction mixture was heated to reflux at 55-60° C. for 1½ h, then cooled down to 0° C. and kept at 0° C. for 16 h. The crystals were filtered off and three times washed with cold 250 ml MTBE.

Yield: 111.8 g (52%), dark yellow crystals.

Step 3: Production of Methyl 2-bromo-5-(2-hydroxyethyl)pyridine-3-carboxylate

Into a 1L three-neck round-bottom flask with a stirrer bar, nitrogen inlet and condenser were added 20 g (78.974 mmol) of methyl-4-(2-acetyloxyethyl)-2-cyano-5-methoxypenta-2,4-dienoate, which was dissolved in 55 ml acetic acid and heated to 35° C. The solution was slowly treated over a period of ½ h with 85.21 g (237 mmol) HBr/HOAc at 35-40° C. with occasional cooling. After the addition was completed the solvents were evaporated at 40° C. and 30 mm Hg and the residue was charged while stirring with a mixture of 60 ml water and 15 ml methanol. The reaction mixture was treated with 3.3 g charcoal and heated for ½ h at 40° C. The charcoal was filtered off and the methanol was distilled off under reduced pressure. The reaction mixture was evaporated and the residue was chromatographed at 100 g silica gel using a solvent mixture of Heptane:Ethyl acetate (2:1 v/v).

Yield: 10.9 g (53%), red oil.

Step 4. Production of Methyl 2-(ethylamino)-5-(2-hydroxyethyl)pyridine-3-carboxylate 7.85 g (30.18 mmol) of methyl 2-bromo-5-(2-hydroxyethyl)pyridine-3-carboxylate (free base) were dissolved in 20 ml MeOH and added to a 250 ml 3-neck-round bottom flask with a stirrer bar, a thermocouple, a addition funnel and a cold condenser (capable for −78° C.). The solution was treated with 433 mg (3.018 mmol, 0.1 equiv.) CuBr and heated to 55-60° C. The reaction mixture was treated dropwise with 74 ml (148 mmol, 4.9 equiv.) 2M EtNH$_2$ in THF. The reaction was kept at 55-60° C. for two hour and monitored. If the chromatogram still shows starting material the reaction was treated with additional 20 ml (40 mmol, 1.32 equiv.) 2M EtNH$_2$ in THF and kept another 2 h at 55-60° C.

To workup the reaction mixture, the solution was evaporated to dryness, dissolved in 20 ml isopropyl acetate and washed with conc. NH$_4$Cl/NaHCO$_3$-solution. Since the reaction product was soluble in water, the aqueous layer was extracted twice with isopropyl acetate, the organic layers were combined, residual water was distilled off as an azeotrope and the solution was filtrated and concentrated to dryness.

Yield: ca. 40-50%, brown oil.

Step 5. Production of 2-(Ethylamino)-5-(2-(4-quinolyloxy)pyridine-3-carboxylic acid Into a 5 liter 3-neck jacketed-flask equipped with a mechanical agitator, thermocouple, and nitrogen inlet were charged 73.84 g 4-Hydroxyquinoline and 146.89 g triphenylphosphine.

Anhydrous DME (1538 ml) was charged to the reactor and the mixture was stirred with slow agitation. The resulting slurry was cooled to ≦20° C. (Jacket=16-18° C.). 139.1 g DIAD (Diisopropyl azodicarboxylate) was added over approximately 1.75 hour while maintaining a temperature of approximately ≦20° C. (During this step the slurry dissolved and reappeared during the addition) The slurry was stirred for an hour at 20-25° C. followed by cooling to ≦-20° C. A solution of methyl 2-(ethylamino)-5-(2-hydroxyethyl)pyridine-3-carboxylate in 1047 ml anhydrous DME was added to the mixture while maintaining a temperature of <-10° C. over 4 hours (-13° C. is highest temperature during this addition). The solution was slowly warmed to 20-25° C. and stirred overnight at 20-25° C. (resulting in a brown solution). The solvent (DME) was removed by distillation under reduced pressure (24-36° C. pot temperature/165-37 mmHg) to give a dark oil. 800 ml of toluene was added to the oil and the resultant solution was extracted with 800 ml of 3N HCl. During the separation it was necessary to warm the mixture to 35-40° C. to ensure that the phases could be separated. The lower acidic aqueous layer was separated and 800 ml of toluene was added. The pH of the mixture was adjusted to 13-14 with 50% sodium hydroxide (~150 ml) while maintaining a temperature between 0-7° C. The mixture was allowed to warm to 20-25° C. Followed by heating to 35-40° C. to separate the aqueous and organic phases. If the toluene solution is stored at this stage; maintain a temperature of 35-40° C. to keep the solution from crystallizing. The toluene was removed by vacuum distillation (35° C./40 mmHg) resulting in a thick slurry. Methanol (1260 ml) was added to the slurry and ~300 ml of distillate was removed by vacuum distillation (35-51° C./133 mmHg) to remove additional toluene. The reaction was cooled to ~15° C.; followed by the addition of sodium hydroxide solution (70 ml of 50% NaOH and 30 ml water) over about 0.5 hours maintaining ≦15° C. Water (49 ml) was added to the mixture while maintaining the temperature at 15° C. The brown solution was stirred for >12 hours at 20-25° C. HPLC analysis showed that all Methyl-2-(ethylamino)-5-(2-(4-quinolyloxy)pyridine-3-carboxylate was converted to 2-(Ethylamino)-5-(2-(4-quinolyloxy)pyridine-3-carboxylic acid. Water (379 ml) was added followed by the removal of methanol (900 ml) by vacuum distillation (20-30° C./133-50 mmHg). The aqueous solution was washed twice with 539 ml of toluene while maintaining a temperature of 35-40° C. Water (476 ml) was added to the mixture along with methanol (79 ml). The solution was heated to 55° C. and the pH adjusted to 6.2±0.2 with 37% HCl (137.86 g) referenced with a Mettler INLAB413 combination electrode. The thick slurry obtained during pH adjustment was slowly cooled to 19-23° C. over ~3 hours and filtered. The light brown solid was washed twice with 381 ml of water at 20-25° C. The product was difficult to de-water due to its characteristics. It was washed with 381 ml of MTBE at 20-25° C. The light brown solid was dried under vacuum for 1 hour at 50° C. and followed by 15 hours at 90° C.

Yield: 149.62 g (60% yield), light brown solid; purity: 99.4 A % (HPLC, 100-% method), $F_p$: 212.5° C.

Step 6. Production of N-(2-Chloro(3-pyridyl))[2-(ethylamino)-5-(2-(4-quinolyloxy)ethyl)(3-pyridyl)]-N-methylcarboxamide In a 3-neck 500 ml flask under N2 was charged 2-(ethylamino)-5-(2-(4-quinolyloxy)pyridine-3-carboxylic acid, 25.0 g and 200 ml of CH$_3$CN. Next, 17.55 g of SOCl$_2$ was charged, over a period of 5-10 minutes at room temperature. An exotherm to ~32° C. was observed. The mixture was stirred at room temperature for about 2-4 hours. A small sample was quenched (with either cyclopropylamine (CPA) or dry MeOH) and checked for completion of in-situ acid chloride formation by HPLC. Excess thionyl chloride was removed by vacuum distillation to about half (90-110 ml) of initial volume after completion of acid chloride formation under pressure (22-28" Hg) below 45° C. The reaction mixture was chased twice with 75 ml CH$_3$CN and residual SOCl$_2$ was removed by distillation. Into the flask was charged acetonitrile 70 ml and the contents of flask was cooled to under 30° C. Next, 2-chloro-3-N-methyl-pyridine 10.56 g was charged neat to the reaction mixture in about 5-10 minutes, followed by a rinse with about 10 ml acetonitrile while keeping temperature below 40° C. The contents of flask were warmed to 45-55° C. The reaction mixture was stirred at 45° C. for about 3 hours and then at 50° C. for about 3 hours. The reaction mixture was quenched with 125 ml of water. The acetonitrile was removed by distillation under reduced pressure while maintaining the temperature below 50° C. Next, 100 ml of ethyl acetate was added to the aqueous layer and the mixture was stirred at room temperature for 5-10 minutes. The organic layer was separated. The aqueous layer was extracted once more with ethyl acetate (20 ml). The organic layer was separated. Next, 1.0 g of activated carbon (Norit-Sx Ultra) was added to the aqueous solution and stirred for about 2 hours at at 22° C. The solution was filtered through a pad of diatomaceous earth (Hyflo supercel). The filter cake was washed with water (2×15 ml). The aqueous layer was extracted with 100 ml of ethyl acetate and the pH adjusted to 12-14 by using 25% NaOH solution, keeping the temperature below 25° C. About 34 g NaOH (25%) was required to achieve the desired pH. The mixture was stirred at room temperature for 5-10 minutes and the organic layer was separated. The aqueous layer was extracted once more with 20 ml of ethyl acetate. The organic extracts were combined and washed with water (2×30 ml). The aqueous layer, which contained unreacted 2-(ethylamino)-5-(2-(4-quinolyloxy)pyridine-3-carboxylic acid, was discarded. The combined EtOAc extract was distilled off under reduce pressure to remove around 60-70 ml of ethyl acetate below 50° C. The mixture was cooled to room temperature while stirring. Crystalline solid appeared during cooling. The mixture was further cooled to around 5-10° C. and held for one hour at 5-10° C. The crystalline solid was filtered and washed with cold ethyl acetate (2×10 ml). The product was dried under vacuum at around 50° C. to a constant weight. The mother liquor was kept for a second crop recovery. The mother liquor was concentrated and cooled to 5-10° C. to obtain the $2^{nd}$ crop. Isolated Yield: $1^{st}$ crop: 23.7.0 g (69.23%); $2^{nd}$ crop: 3.1 g (9.05%); Total yield: 26.8 g (78.28%).

Recrystallization:

The above crude solid (26.8 g) was stirred with 50 ml ethyl acetate and heated to 50-60° C. until dissolved. The mixture was cooled to ~20° C. over a period of about 20-30 minutes. A nice crystalline solid appeared during cooling. The mixture was cooled further to 5-10° C. and held at this temperature for about 1 hour. The solid was filtered and washed with cold ethyl acetate (2×10 ml). The mother liquor was saved for a second crop. The product was dried under vacuum in an oven at 50-60° C. to a constant weight.

Yield: 25.4 g (94.7%), light brown solid, Purity: ~99% (HPLC, 100-% method); $F_p$: 130° C.

Step 7. Production of 5,11-dihydro-11-ethyl-5-methyl-8-{2-(4-quinolinyloxy)ethyl}-6H-dipyrido[3,2-b:2',3'-e][1,4]diazepin-6-one 3.47 g NaOH and 40 ml toluene were charged into a three-neck flask equipped with temperature couple and addition funnel. The mixture was brought to 20° C. Next, 10.02 g of N-(2-chloro(3-pyridyl))[2-(ethylamino)-5-(2-(4-quinolyloxy)ethyl)(3-pyridyl)]-N-methylcarboxamide and 0.7 g tetrabutylammonium bromide were dissolved in 50 ml of toluene at 60-70° C. and allowed to cool to room temperature. The solution of N-(2-chloro(3-pyridyl))[2-(ethylamino)-5-(2-(4-quinolyloxy)ethyl)(3-pyridyl)]-N-methylcarboxamide and TBAB was charged to the addition funnel and slowly added to the slurry from NaOH in Toluene. The reaction mixture was kept at 20-30° C. and stirred overnight. Reaction monitoring was performed with HPLC. During the reaction the product crystallized from the reaction mixture. In the event that the reaction had not completed after 16 h the reaction mixture was heated up to 30° C. and kept there until the reaction was complete. The reaction mixture was quenched with 25 ml saturated NH$_4$Cl solution. A temperature increase from 20.8° C. to 25.5° C. was observed. The reaction mixture was heated to 85-90° C. The precipitate dissolved upon heating and a slow release of a gas (Ammonia) was observed. Phase separation at 85-90° C. was performed. The lower aqueous layer was analyzed for product and pH (target: pH=6) and then discarded. 41 ml of toluene/water (about 40 ml toluene, 1 ml water) was azeotropically distilled off the solution under reduced pressure. The solution was slowly cooled to room temp., then to 0° C. and stirred for at least 30 min at 0° C. to complete crystallization. The crystals were collected by filtration and washed twice with 10 ml of cooled toluene at 0° C. Crude Yield: 8.436 g; yellowish to off-white crystals. The off-white to yellow product was dried at 50° C. under vacuum over night.

The crude product was slurried in 48 ml of toluene and heated to reflux. A solution was formed at about 70-80° C. The solution was filtered hot to remove inorganic and mechanical impurities. The solution was slowly cooled first to room temperature, then to 0° C., stirred for 30 min-1 h and filtered. The crystals were collected and washed twice each with 10 ml cooled toluene (0-3° C.). The collected crystals were dried overnight at 50° C. under vacuum.

Yield: 6.7-7.2 g white to off-white solid, Chromatographic purity: ca. 96%, 70-75% yield

What is claimed is:

1. A process for making 5,11-dihydro-11-ethyl-5-methyl-8-{2-{(1-oxido-4-quinolinyl)oxy}ethyl}-6H-di pyrido[3,2-b:2',3'-e][1,4]diazepin-6-one, which process comprises the following steps:

(a) reacting 2,3-dihydrofuran with a trialkylorthoformate of the formula

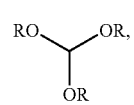

wherein each of the groups R is selected independently and is an alkyl of 1 to 6 carbon atoms, phenyl or cycloalkyl group of 3 to 6 carbon atoms, in the presence of a catalytic amount of an acid, to yield an intermediate of the formula

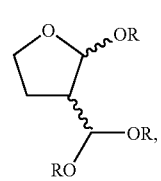

wherein R is as hereinbefore defined;

(b) reacting the intermediate of the formula II, formed in the preceding step, with an acid anhydride of the formula

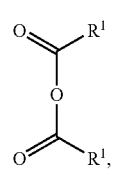

wherein each $R^1$ group is an alkyl group of 2 to 6 carbon atoms, cycloalkyl of 3 to 6 carbon atoms, phenyl or benzyl, in the presence of a catalytic amount of a Lewis acid, and with an alkylcyanoacetate of the formula

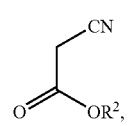

wherein $R^2$ is an alkyl group of 2 to 6 carbon atoms, cycloalkyl of 3 to 6 carbon atoms, phenyl or benzyl, to yield a substituted penta-2,4-dienenitrile intermediate of the formula

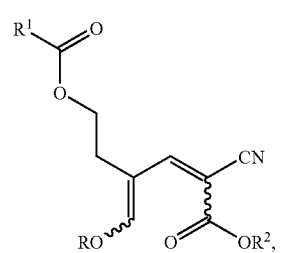

wherein the groups R, $R^1$ and $R^2$ are as hereinbefore defined;

(c) dissolving the substituted penta-2,4-dienenitrile intermediate of the formula V, obtained from the prior step, in a suitable carboxylic acid, and treating it with an anhydrous acid of the formula HX, wherein X is a halogen atom, to yield a substituted pyridine of the formula

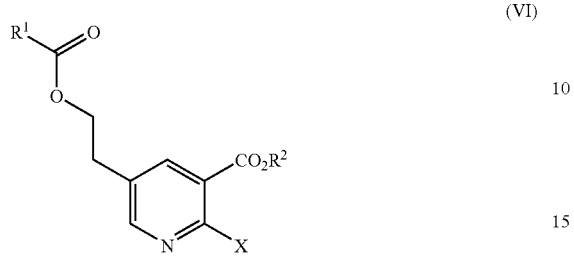

(VI)

wherein $R^1$, $R^2$ and X are as hereinbefore defined;

(d) treating the substituted pyridine of the formula VI, obtained from the previous step, with an alcohol of the formula $R^3OH$, wherein $R^3$ is an alkyl group of 2 to 6 carbon atoms, cycloalkyl of 3 to 6 carbon atoms, phenyl or benzyl, to yield a saponified intermediate of the formula

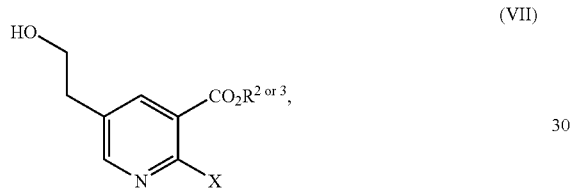

(VII)

wherein $R^2$, $R^3$ and X are as hereinbefore defined;

(e) reacting the substituted pyridine of the formula VII, obtained from the preceding step, with ethylamine, in the presence of a catalyst, to yield an aminated intermediate of the formula

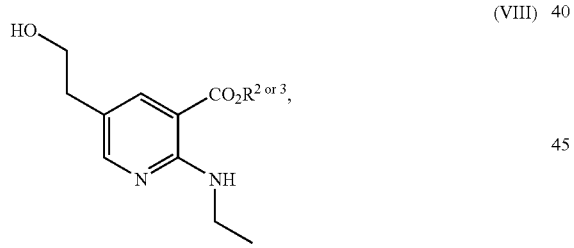

(VIII)

wherein $R^2$ and $R^3$ are as hereinbefore defined;

(f) reacting the intermediate of the formula VIII, obtained from the previous step, with 4-hydroxyquinoline, in the presence of a reagent which generates a suitable leaving group from the alcoholic moiety of the compound of the formula VIII, to yield an intermediate of the formula

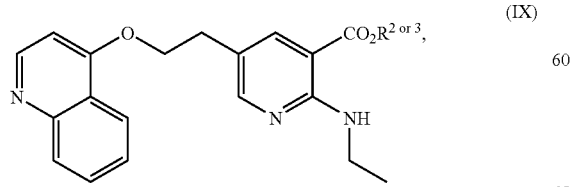

(IX)

wherein $R^2$ and $R^3$ are as hereinbefore defined;

(g) hydrolyzing the ester intermediate of the formula IX, obtained from the previous step, to yield the carboxylic intermediate of the formula

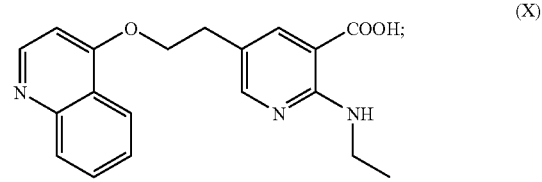

(X)

(h) reacting the carboxylic acid intermediate of the formula X, obtained from the previous step, with an activating agent, to yield an activated acid of the formula XI

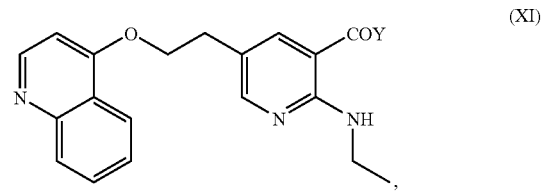

(XI)

wherein Y is $OR^4$ (wherein $R^4$ is a leaving group) or a halogen;

(i) reacting the activated acid of the formula XI, obtained from the previous step, with 2-chloro-3-methylaminopyridine, to yield a further intermediate of the formula

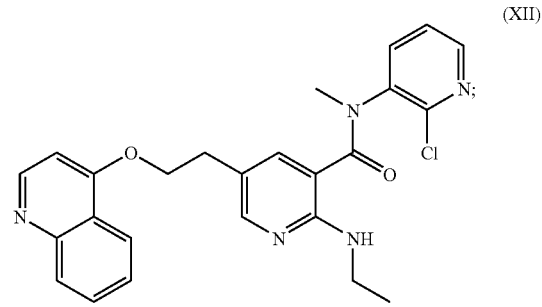

(XII)

(j) treating the intermediate of the formula XII, obtained from the previous step, with base, to induce ring closure and yield the intermediate of the formula

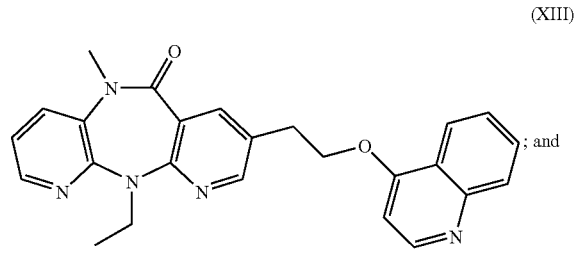

(XIII)

; and (k) treating the intermediate of the formula XIII with an oxidizing agent to yield the final product, 5,11-dihydro-11-ethyl-5-methyl-8-{2-{(1-oxido-4-quinolinyl)oxy}ethyl}-6H-di pyrido[3,2-b:2',3'-e][1,4]diazepin-6-one.

2. The process of claim 1 wherein the acid employed as solvent in step (c) is acetic acid.

3. The process of claim 1 wherein the catalyst employed in step (e) is selected from the group consisting of copper (I) chloride, copper (I) bromide, copper (I) iodide, copper (I)

triflate, copper (I) oxide, copper (II) chloride, copper (II) bromide, copper (II) iodide and copper (II) oxide or it is a palladium catalyst.

4. The process of claim 1 wherein, in step (f), Mitsunobu conditions are employed to generate a suitable leaving group from the alcoholic moiety of the compound of the formula VIII.

5. The process of claim 1 wherein, in step (h), Y is $OR^4$ (wherein $OR^4$ is OBt, ONSu or OPFP), or $O_2CR^5$ (wherein $R^5$ is an alkyl group of 2 to 6 carbon atoms, cycloalkyl of 3 to 6 carbon atoms, phenyl or benzyl).

6. The process of claim 1 wherein, in step (h), the activating agent is a halogenating reagent selected from the group consisting of phosphorous oxychloride, phosphorous trichloride, phosphorous pentachloride, cyanuric chloride, oxalylchloride and thionyl chloride.

7. A compound of the formula

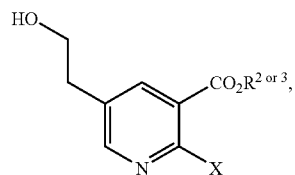

(VII)

wherein $R^2$ and $R^3$ are each, independently, an alkyl group of 2 to 6 carbon atoms, cycloalkyl of 3 to 6 carbon atoms, phenyl or benzyl; and, X is a halogen atom.

8. A compound of the formula

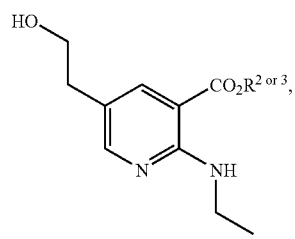

(VIII)

wherein $R^2$ and $R^3$ are each, independently, an alkyl group of 2 to 6 carbon atoms, cycloalkyl of 3 to 6 carbon atoms, phenyl or benzyl.

9. A compound of the of the formula

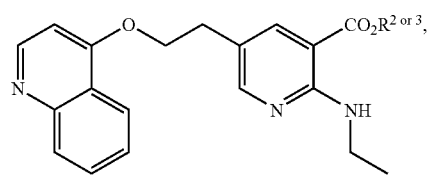

(IX)

wherein $R^2$ and $R^3$ are each, independently, an alkyl group of 2 to 6 carbon atoms, cycloalkyl of 3 to 6 carbon atoms, phenyl or benzyl.

10. The compound of the formula

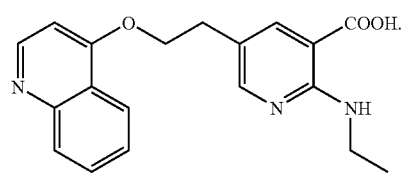

(X)

11. The compound of the formula

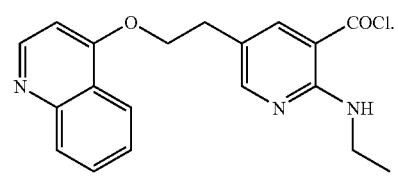

(XI)

12. The compound of the formula

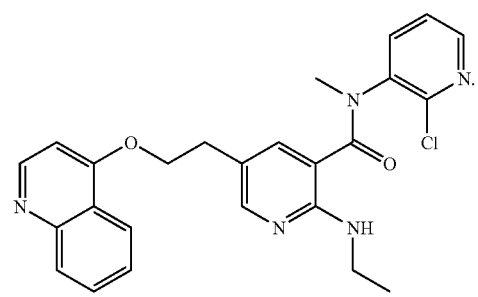

(XII)

13. A process for making 5,11-dihydro-11-ethyl-5-methyl-8-{2-{(1-oxido-4-quinolinyl)oxy}ethyl}-6H-di pyrido [3,2-b:2',3'-e][1,4]diazepin-6-one, which process comprises the following steps:

(a) hydrolyzing an ester intermediate of the formula IX

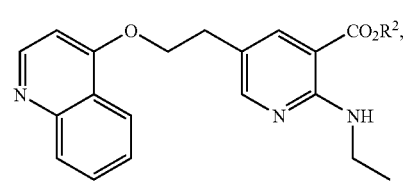

(IX)

wherein $R^2$ is an alkyl group of 2 to 6 carbon atoms, cycloalkyl of 3 to 6 carbon atoms, phenyl or benzyl, to yield the carboxylic intermediate of the formula

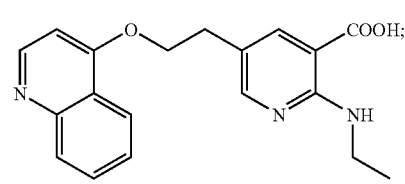

(X)

(b) reacting the carboxylic acid intermediate of the formula X, obtained from the previous step, with an activating agent, to yield an activated acid of the formula XI

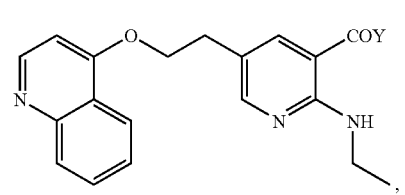

(XI)

wherein Y is $OR^4$ (wherein $R^4$ is a leaving group) or a halogen;

(c) reacting the activated acid of the formula XI, obtained from the previous step, with 2-chloro-3-methylaminopyridine, to yield a further intermediate of the formula

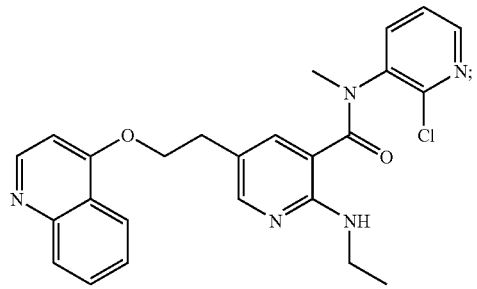
(XII)

(d) treating the intermediate of the formula XII, obtained from the previous step, with base, to induce ring closure and yield the intermediate of the formula

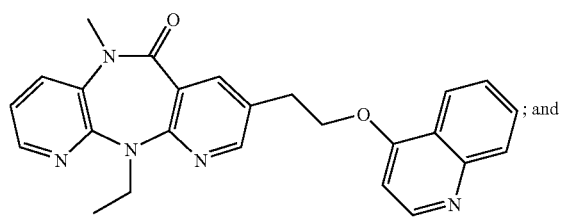
(XIII); and (e) treating the intermediate of the formula XIII with an oxidizing agent to yield the final product, 5,11-dihydro-11-ethyl-5-methyl-8-{2-{(1-oxido-4-quinolinyl)oxy}ethyl}-6H-di pyrido[3,2-b:2',3'-e][1,4]diazepin-6-one.

14. A process for making 5,11-dihydro-11-ethyl-5-methyl-8-{2-{(1-oxido-4-quinolinyl)oxy}ethyl}-6H-di pyrido[3,2-b:2',3'-e][1,4]diazepin-6-one, which process comprises the following steps:

(a) reacting the carboxylic acid of the formula X,

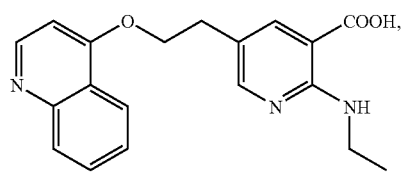

with an activating agent, to yield an activated acid of the formula XI

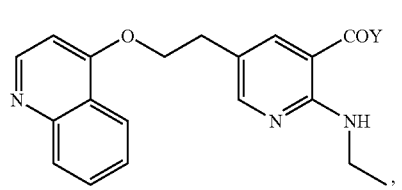
(XI)

wherein Y is $OR^4$ (wherein $R^4$ is a leaving group) or a halogen;

(b) reacting the activated acid of the formula XI, obtained from the previous step, with 2-chloro-3-methylaminopyridine, to yield a further intermediate of the formula

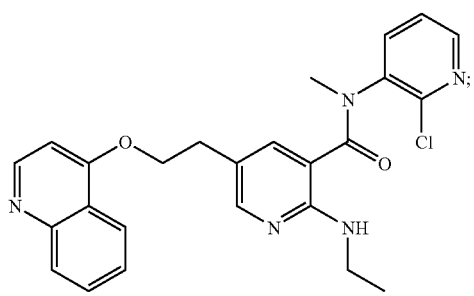
(XII)

(c) treating the intermediate of the formula XII, obtained from the previous step, with base, to induce ring closure and yield the intermediate of the formula

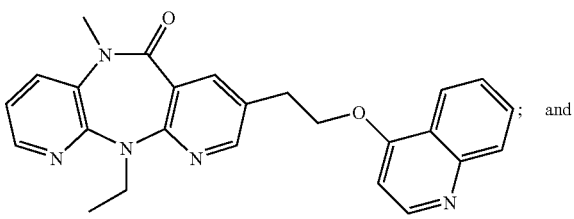
(XIII); and (d) treating the intermediate of the formula XIII with an oxidizing agent to yield the final product, 5,11-dihydro-11-ethyl-5-methyl-8-{2-{(1-oxido-4-quinolinyl)oxy}ethyl}-6H-di pyrido[3,2-b:2',3'-e][1,4]diazepin-6-one.

15. A process for making 5,11-dihydro-11-ethyl-5-methyl-8-{2-{(1-oxido-4-quinolinyl)oxy}ethyl}-6H-di pyrido[3,2-b:2',3'-e][1,4]diazepin-6-one, which process comprises the following steps:

(a) reacting an activated acid of the formula XI

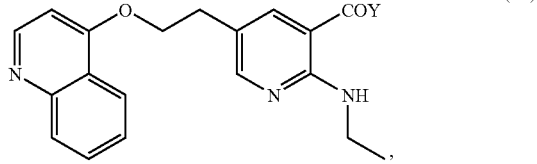
(XI)

wherein Y is $OR^4$ (wherein $R^4$ is a leaving group) or a halogen, with 2-chloro-3-methylaminopyridine, to yield an intermediate of the formula (XII)

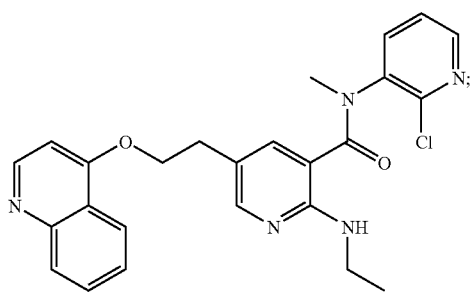

(b) treating the intermediate of the formula XII, obtained from the previous step, with base, to induce ring closure and yield the intermediate of the formula (XIII)

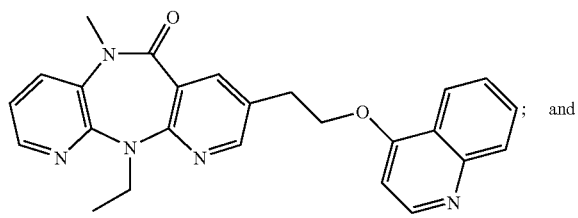

(c) treating the intermediate of the formula XIII with an oxidizing agent to yield the final product, 5,11-dihydro-11-ethyl-5-methyl-8-{2-{(1-oxido-4-quinolinyl)oxy}ethyl}-6H-di pyrido[3,2-b:2',3'-e][1,4]diazepin-6-one.

16. A process for making 5,11-dihydro-11-ethyl-5-methyl-8-{2-{(1-oxido-4-quinolinyl)oxy}ethyl}-6H-di pyrido[3,2-b:2',3'-e][1,4]diazepin-6-one, which process comprises the following steps:

(a) treating the compound of the formula (XII)

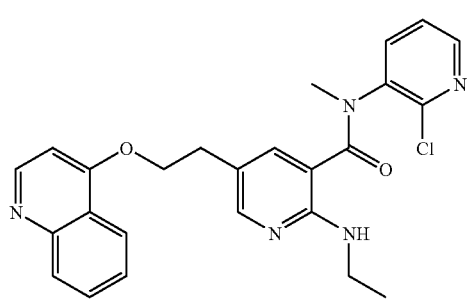

with base to induce ring closure and yield the intermediate of the formula (XIII)

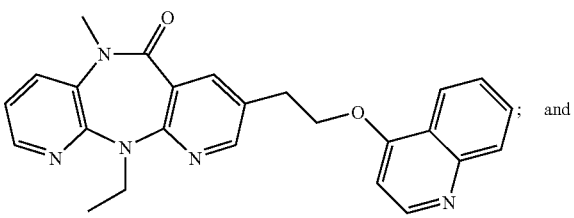

(b) treating the intermediate of the formula XIII with an oxidizing agent to yield the final product, 5,11-dihydro-11-ethyl-5-methyl-8-{2-{(1-oxido-4-quinolinyl)oxy}ethyl}-6H-di pyrido[3,2-b:2',3'-e][1,4]diazepin-6-one.

* * * * *